United States Patent
Headley, Jr. et al.

(10) Patent No.: US 7,594,928 B2
(45) Date of Patent: Sep. 29, 2009

(54) BIOABSORBABLE STENTS WITH REINFORCED FILAMENTS

(75) Inventors: F. Anthony Headley, Jr., Marlborough, MA (US); Kurt Geitz, Sudbury, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 92 days.

(21) Appl. No.: 11/436,067

(22) Filed: May 17, 2006

(65) Prior Publication Data

US 2007/0270941 A1  Nov. 22, 2007

(51) Int. Cl.
*A61F 2/88* (2006.01)

(52) U.S. Cl. .................. 623/1.22; 623/1.38

(58) Field of Classification Search .......... 623/1.22, 623/1.38
See application file for complete search history.

(56) References Cited

U.S. PATENT DOCUMENTS

| | | | |
|---|---|---|---|
| 4,671,280 A | 6/1987 | Dorband et al. | 128/334 |
| 4,954,126 A | 9/1990 | Wallsten | 600/36 |
| 4,968,317 A | 11/1990 | Tormala et al. | 606/77 |
| 5,234,457 A | 8/1993 | Andersen | 606/198 |
| 5,248,305 A | 9/1993 | Zdrahala | |
| 5,366,504 A | 11/1994 | Andersen et al. | 623/11 |
| 5,792,400 A | 8/1998 | Talja et al. | 264/103 |
| 5,800,519 A * | 9/1998 | Sandock | 623/1.22 |
| 6,171,338 B1 | 1/2001 | Talja et al. | 623/11.11 |
| 6,245,103 B1 | 6/2001 | Stinson | 623/1.22 |
| 6,305,436 B1 | 10/2001 | Andersen et al. | 140/107 |
| 6,503,278 B1 | 1/2003 | Pohjonen et al. | 623/16.11 |
| 6,709,452 B1 | 3/2004 | Valimaa et al. | 623/1.15 |
| 6,776,945 B2 * | 8/2004 | Chin et al. | 264/171.26 |
| 7,128,862 B2 * | 10/2006 | Wang | 264/171.29 |
| 7,161,608 B2 * | 1/2007 | Pettitt et al. | 345/690 |
| 2003/0009114 A1 * | 1/2003 | Chin et al. | 600/585 |
| 2003/0009151 A1 * | 1/2003 | Wang | 604/526 |
| 2003/0014127 A1 | 1/2003 | Talja et al. | 623/23.75 |
| 2003/0083745 A1 | 5/2003 | Pohjonen et al. | 623/11.11 |
| 2003/0100869 A1 * | 5/2003 | Wang | 604/264 |
| 2003/0204235 A1 | 10/2003 | Edens et al. | |
| 2003/0236514 A1 | 12/2003 | Schwarz | 604/890.1 |
| 2004/0148014 A1 * | 7/2004 | Nuutinen et al. | 623/1.15 |
| 2004/0236310 A1 * | 11/2004 | Chin et al. | 604/523 |

FOREIGN PATENT DOCUMENTS

| | | |
|---|---|---|
| EP | 0894505 A | 2/1999 |
| WO | 9909911 A | 3/1999 |
| WO | 2005003300 A | 1/2005 |

OTHER PUBLICATIONS

D.P. Faxon, "Biodegradable Stents: Are They Finally Here?," *Reviews in Cardiovascular Medicine*, vol. 2, No. 2 (2001): 106-107.

* cited by examiner

*Primary Examiner*—Thomas J Sweet
(74) *Attorney, Agent, or Firm*—Mayer & Williams PC; David B. Bonham, Esq.

(57) ABSTRACT

According to an aspect of the present invention, a stent is provided, which contains at least one filament that has a longitudinal axis and comprises a bioabsorbable polymeric material. Polymer molecules within the bioabsorbable polymeric material are provided with a helical orientation which is aligned with respect to the longitudinal axis of the filament. The stent is at least partially bioabsorbed by a patient upon implantation or insertion of the stent into the patient.

17 Claims, 4 Drawing Sheets

BIOABSORBABLE STENTS WITH REINFORCED FILAMENTS

BACKGROUND OF THE INVENTION

Bioabsorbable stents are a key development focus for many medical device companies because they are expected to eliminate many of the long-term issues that may arise from the use of biostable stents.

Key limitations of bioabsorbable stents are the physical limitations of the as-processed bioabsorbable materials, including the mechanical strength or the same. The mechanical properties of bioabsorbable materials have been enhanced previously by utilizing a process that is commonly referred to as "self reinforcement" or "orientrusion" wherein the material is drawn in a manner such that the polymer strands within the filament become aligned with the axis of the filament. Such processes are known to produce tensile modulus of approximately 2 GPa to 8 GPa for materials such as polymers and copolymers of polylactide (PLA), including poly-L-lactide (PLLA), poly-D-lactide (PDLA), poly-DL-lactide (PDLLA).

SUMMARY OF THE INVENTION

The present invention describes a novel way to enhance the material properties of stents that are formed of bioabsorbable filaments.

According to an aspect of the present invention, a stent is provided that contains at least one filament, which filament has a longitudinal axis and comprises a bioabsorbable polymeric material. Polymer molecules within the bioabsorbable polymeric material are provided with a helical orientation which is aligned with respect to the longitudinal axis of the filament. The stent is at least partially bioabsorbed by a patient upon implantation or insertion of the stent into the patient.

Advantages of the present invention are that stents are provided which may have one or more of the following properties: increased radial force, decreased filament diameter for a given stent size, improved resistance to creep, and increased material selection due to improvement in properties.

These and other aspects, embodiments and advantages of the present invention will become immediately apparent to those of ordinary skill in the art upon review of the Detailed Description and Claims to follow.

DETAILED DESCRIPTION OF THE INVENTION

The present invention is directed to stents that are bioabsorbed by a patient upon implantation or insertion of the stent into the patient. The stents of the present invention are adapted for deployment at various placement sites within the patient, and include vascular stents (e.g., coronary vascular stents and peripheral vascular stents such as cerebral stents), urinary stents (e.g., urethral stents and ureteral stents), biliary stents, tracheal stents, gastrointestinal stents and esophageal stents.

The stents of the present invention contain one or more filaments (also referred to herein as "oriented filaments"), which in turn contain an oriented bioabsorbable polymeric material (also referred to herein as "oriented material"). The polymer molecules within the oriented bioabsorbable polymeric material have a helical orientation with an axis that is which is aligned with respect to (e.g., the axes of the helices are parallel to) the longitudinal axis of the filament. As indicated further below, the oriented bioabsorbable polymeric material may be formed from a single type of polymer (e.g., from PLLA, PGA, etc.) or from a blend of two or more polymer types (e.g., from a blend of PLLA and PGA, etc.). Preferably, the oriented bioabsorbable polymeric material is somewhat crystalline, in which case the fibrils (i.e., bundles of crystalline polymer chains) within the material are likewise oriented in a helical fashion.

In the present invention, the molecules and/or fibrils within the oriented bioabsorbable polymeric material are oriented in order to improve both the bending and torsional rigidity of the filaments, relative to filaments containing non-oriented bioabsorbable polymeric material. Such filaments may be employed in a wide variety of filament based stents, in accordance with the present invention, including stents formed using a variety of wire forming techniques, such as coiling techniques and woven techniques (e.g., braiding or knitting), particularly stents which contain coiled and/or braided filaments, since the filaments of these devices are placed under both torsional and bending stresses.

The stents of the present invention may contain multiple oriented filaments. These filaments may contain oriented material that is formed from the same type of polymer or polymer blend (e.g., each filament having oriented material formed from PLLA, each having oriented material formed from a blend of PLLA and PGA, etc.), or they may contain oriented material that is formed from differing polymers or polymer blends (e.g., one filament having oriented material formed from PLLA and another having oriented material formed from PGA, one filament having oriented material formed from PLLA and another having oriented material formed from PLLA/PGA, etc.). Moreover, the one or more oriented filaments may be formed (a) entirely of oriented material or (b) partially of oriented material, for example, (i) having a core of oriented bioabsorbable polymeric material and a coating of oriented bioabsorbable polymeric material, (ii) having a core of oriented bioabsorbable polymeric material and a coating of a bioabsorbable polymeric material that is not oriented, (iii) having a core of non-bioabsorbable material and a coating of oriented bioabsorbable polymeric material, (iv) and so forth.

In addition to one or more oriented filaments, additional filaments may be provided within the stents of the present invention which do not contain an oriented bioabsorbable polymeric material, including filaments that are formed a bioabsorbable polymeric material whose polymer molecules are not helically oriented and/or filaments that are formed from a non-bioabsorbable material. For example, such additional filaments may be provided, along with the oriented filaments of the invention, in a coiled, braided, or knitted arrangement, among others.

Moreover, the oriented filaments in accordance with the present invention may include a therapeutic agent in some embodiments, for example, (a) disposed within the filament or attached to the surface of the filament or (b) where the filament is provided with the a coating, disposed within or attached to the coating. The therapeutic agent may be covalently linked to another species such as a polymer molecule or it may be in free form (i.e., not covalently linked to another species, although other attractive/binding forces may be present such as Van der Waals forces, ionic forces, hydrogen bonding, coordination bonding, ionic-coordination bonding or physical entrapment).

"Therapeutic agents," "drugs," "bioactive agents," "pharmaceuticals," "pharmaceutically active agents", and other related terms may be used interchangeably herein and include genetic therapeutic agents, non-genetic therapeutic agents, and cells. Therapeutic agents may be used singly or in combination. A wide range of therapeutic agent loadings can be used in conjunction with the devices of the present invention, with the pharmaceutically effective amount being readily determined by those of ordinary skill in the art and ultimately depending, for example, upon the condition to be treated, the nature of the therapeutic agent itself, the tissue into which the dosage form is introduced, and so forth.

Some specific beneficial agents include anti-thrombotic agents, anti-proliferative agents, anti-inflammatory agents, anti-migratory agents, agents affecting extracellular matrix production and organization, antineoplastic agents, anti-mitotic agents, anesthetic agents, anti-coagulants, vascular cell growth promoters, vascular cell growth inhibitors, cholesterol-lowering agents, vasodilating agents, and agents that interfere with endogenous vasoactive mechanisms.

More specific agents include paclitaxel, sirolimus, everolimus, tacrolimus, Epo D, dexamethasone, estradiol, halofuginone, cilostazole, geldanamycin, ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, and Serca 2 gene/protein, resiquimod, imiquimod (as well as other imidazoquinoline immune response modifiers), human apolioproteins (e.g., AI, AII, AIII, AIV, AV, etc.), vascular endothelial growth factors (e.g., VEGF-2), as well a derivatives of the forgoing, among many others.

Numerous additional therapeutic agents useful for the practice of the present invention may be selected from those described in paragraphs [0040] to [0046] of commonly assigned U.S. Patent Application Pub. No. 2003/0236514, the entire disclosure of which is hereby incorporated by reference.

One such stent design, which employs one or more oriented filaments of the present invention, will now be described in conjunction with FIGS. 1A through 3B. An analogous design, albeit without the oriented filaments of the present invention, is described in U.S. Pat. No. 4,954,126 to Walstén.

Figure 1A:
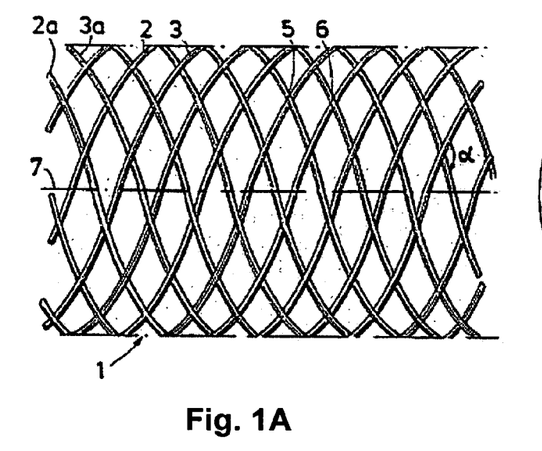
FIGS. 1A and 1B are side and end views of a stent, in accordance with an embodiment of the present invention.
Figure 1B:
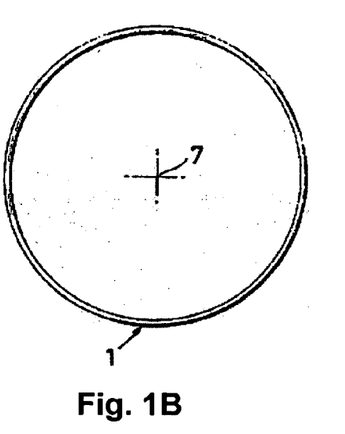

Referring now to these figures, in FIGS. 1A and 1B there is shown in an example of a stent in the form of a cylindrical tubular body generally designated by the numeral 1. Body 1 is formed by a number of filaments 2, 3, etc. and 2a, 3a etc. Of these, filaments 2, 3 etc. are in the form of helices which are axially displaced in relation to each other and have the center line 7 of the body 1 as a common axis. The other filaments 2a, 3a are also in the form of helices, which are axially displaced in relation to each other and have the center line 7 of body 1 as a common axis; however, these helices extend in the opposite direction relative to helices 2, 3, etc. The filaments extending in the two directions cross each other at points 5, 6, etc. in the manner indicated in FIG. 1A.

The ends of the body 1 are axially displaced relative to each other in the direction of the center line 7 as the diameter of the tubular body 1 is varied. For example, in FIG. 2A there is illustrated how the tubular body 1 according to FIG. 1A is reduced in diameter as ends 8, 9 move away from each other in the direction of the arrows. FIG. 1B shows the diameter of the tubular body 1 in an expanded state, whereas FIG. 2B shows the diameter of body 1 in a contracted state.

Figure 2A:
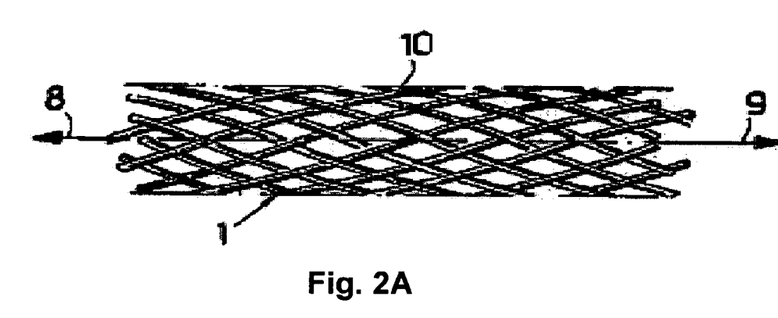
FIGS. 2A and 2B are side and end views of the stent of FIGS. 1A and 1B, subsequent to a reduction in the diameter of the same.
Figure 2B:
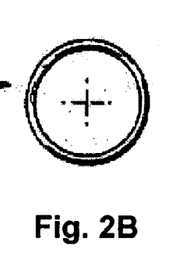
Figure 3A:
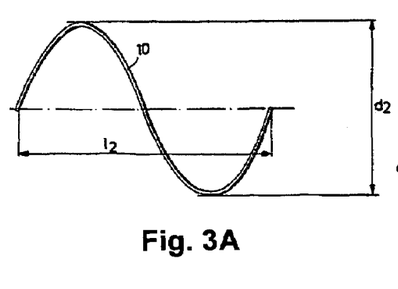
FIGS. 3A and 3B are helical elements from the stents of FIGS. 1A and 2A, respectively.
Figure 3B:
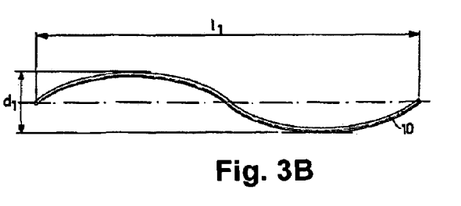

FIGS. 3A and 3B show a detail from FIGS. 1A and 2A, more particularly a single filament of the tubular body 1 and how its helical configuration is changed in conjunction with a change of the length of the tubular body 1. (A typical device will comprise between 12 to 36 helical filaments, but more or less filaments can obviously be used. As previously indicated, all or only a portion of the filaments within the stent may be oriented filaments. Moreover, oriented filaments may differ from one another, for example, with respect to polymer content or in various other ways, including those previously described.)

In FIG. 3B the individual filament 10 corresponding to filament 10 of FIG. 2A is shown. The diameter of the helix is $d_1$ and the length of the filament is $l_1$. In FIG. 3A the same filament 10 is shown after the tubular body diameter has been expanded to the state shown in FIG. 1A. The diameter of the helix has now increased and is designated $d_2$, whereas the length has decreased and is designated $l_2$.

The tubular body 1 can be expanded in a number of ways. In general, it is preferred that the body 1 inherently have the property of taking expanded position by itself in unloaded condition, for example, due to the inherent elasticity of the filaments.

It is noted that WALLSTENT® Stent System, currently sold by Boston Scientific Corporation, is an example of a braided stent of the general type illustrated in FIG. 1A. This stent is formed form stainless steel filaments and its design gives it a number of desirable features, including the following: it has high longitudinal flexibility for negotiating tortuous body lumens; it has radial elasticity, allowing it to undergo compression without permanent deformation (i.e., it can self-expand from a compressed state); and it has high hoop strength. However, unlike the stents of the present invention, it is not wholly or partially bioabsorbable.

Figure 4:
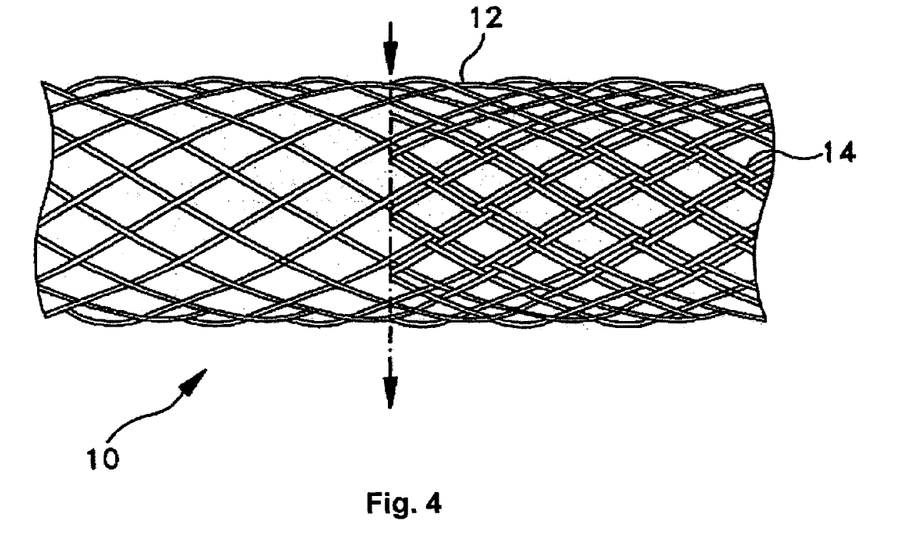
FIG. 4 illustrates a multi-filament variation on the stent design of FIG. 1A, in accordance with an embodiment of the present invention.

FIG. 4 illustrates a variation of the stent shown in FIG. 1A. In particular, a tubular body 10 is illustrated in FIG. 4. On the left side of the arrows in FIG. 4, the body 10 is illustrated as being composed of simple helical filaments as in FIG. 1A above. The body 10 on the right side of the arrows, however, is of a more complex braided design in which sets of three filaments 12 are combined to form the axially spaced helical elements 14. One, two or all three of the filaments 12 within these elements 14 may be oriented filaments. Moreover, where multiple oriented filaments are employed, they may differ from one another, for example, with respect to polymer content or in various other ways including those previously described.

Another braided stent design employing one or more oriented filaments of the present invention will now be described in connection with FIGS. 5A through 7C. An analogous design, albeit without the oriented filaments of the present invention, is described in U.S. Pat. No. 5,800,519 to Sandock.

Figure 5A:
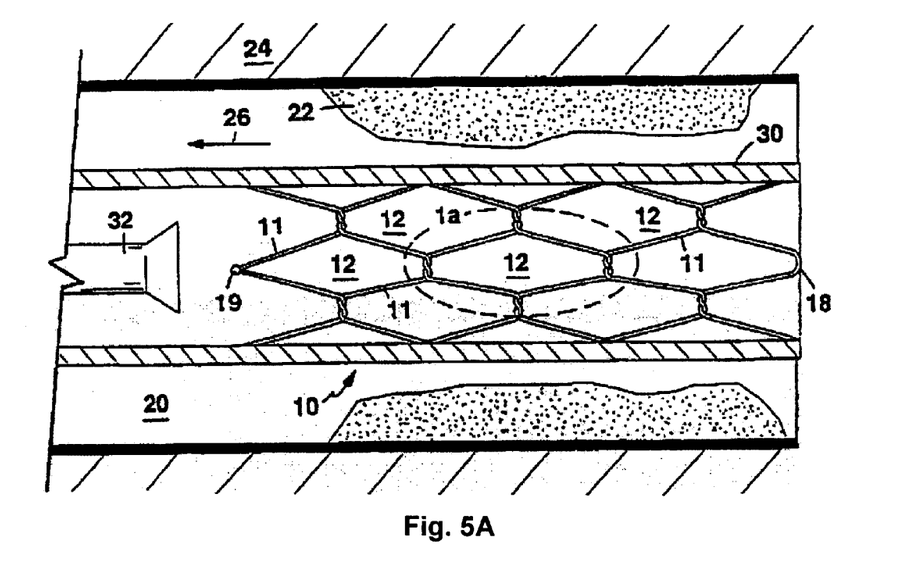
FIGS. 5A to 5C schematically illustrate the deployment of a stent, in accordance with another embodiment of the invention.
Figure 5B:
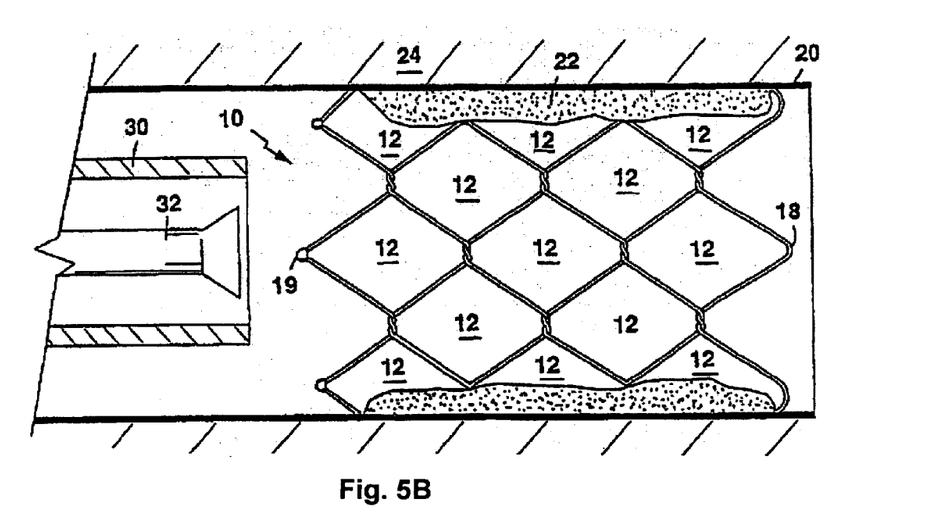
Figure 5C:
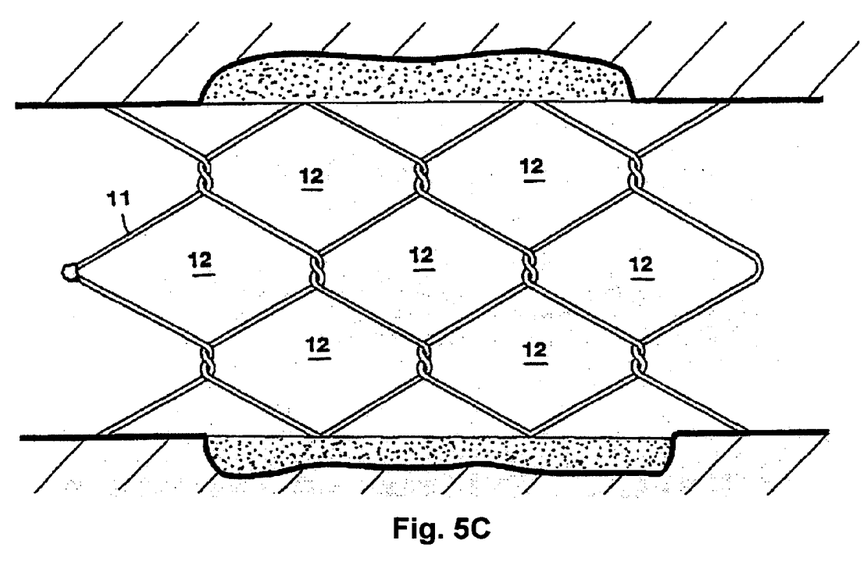

Referring now to FIGS. 5A-5C, a self-expanding stent 10 in accordance with the present invention is shown in different stages of expansion. The stent has a proximal end 19 and a distal end 18 and is formed of oriented filaments 11 in accordance with the present invention which are arranged to form a pattern of geometric diamond-shaped cells 12 (see cell 12, within oval 1a). The sides of the cells are defined by filament lengths that meet at regions of intersection. At the regions of intersection, the strands are helically wrapped about each other to form interlocking joints. The interlocking joints are arranged so that the axes of the helices extend in the circumferential direction and are substantially in the plane of the stent wall.

Referring now to FIG. 5A, the stent is introduced into a body lumen 20 to the site of deployment inside a sleeve 30 that maintains the stent in a compressed, reduced size. Depending on delivery site, the stent may be delivered over a guide wire, through the working channel of an endoscope, etc. Referring now to FIG. 5B, when a catheter carrying the stent is positioned within the body lumen at a site corresponding to an obstruction, such as, for example, occlusion 22, the sleeve 30 is withdrawn in the direction of arrow 26, enabling the stent 10 to radially expand by its own internal restoring forces and engage the occlusion as well as the adjacent healthy wall of the lumen. (A member 32 is used in the embodiment illustrated to maintain the axial position of the stent 10 as the sleeve is retracted.) Referring to FIG. 5C, after deployment, the stent expands and pushes the lumen walls outward to open the lumen.

The Ultraflex™ Precision Colonic Stent System, currently sold by Boston Scientific Corporation, is an example of a braided stent of the general type illustrated in FIGS. 5A-5C. This stent is formed form nitinol wire and its design gives it a number of desirable features, including the fact that it has high longitudinal flexibility for negotiating tortuous body lumens and it has radial elasticity, allowing it to undergo compression without permanent deformation. However, unlike the stents of the present invention, it is not wholly or partially bioabsorbable.

Other braided stent designs are known besides those described above, within which oriented filaments in accordance with the present invention may be incorporated, including the Expander™ from Medicorp and WallFlex™ from Boston Scientific Corporation.

A knitted stent design employing the filaments of the present invention will now be described in connection with FIG. 6. Analogous designs, albeit without one or more oriented filaments of the present invention, are described in U.S. Pat. No. 5,234,457 to Anderson, U.S. Pat. No. 5,366,504 to Anderson and Strecker, and U.S. Pat. No. 6,305,436 to Anderson et al. (In general, braided stents are considered to be better than knitted stents from a self-expansion standpoint, whereas knitted stents are generally considered to be more immune from shortening during expansion.)

Figure 6:
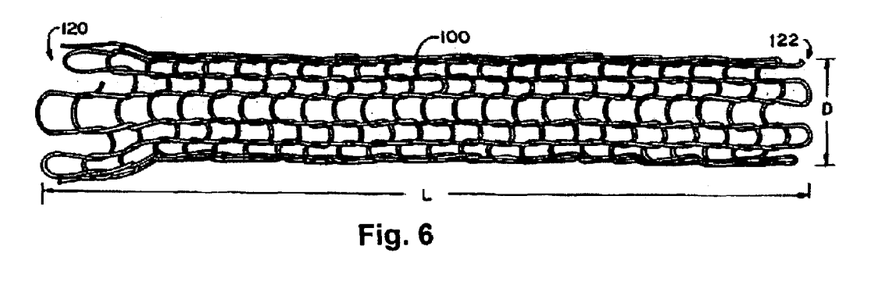
FIG. 6 is a side view of a stent, in accordance with yet another embodiment of the present invention.

FIG. 6 illustrates a stent which comprises a filament 100 that is knitted into a mesh cylinder having a length L and a diameter D, with opposing ends 120 and 122. The mesh cylinder is formed from a fabric of loosely interlocked filament loops that form the wall of the same.

The Strecker™ vascular stent, Boston Scientific Corporation, is an example of a knitted stent of the general type illustrated in FIG. 6. This stent is formed form tantalum wire and its design gives it a number of desirable features, including the following: it has high longitudinal flexibility for negotiating tortuous body lumens; and its shortening during expansion is slight. Other knitted stent designs are known, including the Wiktor™ from Medtronic and the ZA™ Stent from Cook. However, unlike the stents of the present invention, these stents are not wholly or partially bioabsorbable.

The stents of the present invention generally assume a substantially tubular form in both a contracted and an expanded state. In certain embodiments, the stents are self-expanding, by which is meant that they return to an expanded state when released from a compressed state (for instance, when they are compressed into a sheath and released from the sheath in vivo). In many instances, however, the stents of the present invention may benefit from additional outward radial expansion forces during deployment (for instance, using a balloon or other stent-expanding device known in the art).

As indicated above, the oriented filaments used in conjunction with the present invention contain an oriented bioabsorbable polymeric material. By "polymeric material" is meant a material that contains either a single type of polymer or a blend of two or more types of polymers. The bioabsorbable polymers employed herein may be homopolymers or copolymers, and take on a variety of architectures, although linear architectures are preferred.

Examples of bioabsorbable polymers for the practice of the present invention include suitable polymers selected from the following: poly(alpha-hydroxy acid) polymers and copolymers, such as polymers and copolymers of glycolide including polyglycolide (PGA), poly(glycolide-co-lactide) (PGLA), and poly (glycolide-co-trimethylene carbonate (PGA/TMC; polymers and copolymers of polylactide (PLA) including poly-L-lactide (PLLA), poly-D-lactide (PDLA), poly-DL-lactide (PDLLA), poly(lactide-co-tetramethylene glycolide), poly(lactide-co-trimethylene carbonate), poly (lactide-co-delta-valerolactone), poly(lactide-co-epsilon-caprolactone), poly(glycine-co-DL-lactide) and poly(lactide-co-ethylene oxide); polydioxanone polymers such as asymmetrically 3,6-substituted poly-1,4-dioxane-2,5-diones; poly(beta-hydroxybutyrate) (PHBA) and copolymers of the same such as poly(beta-hydroxybutyrate-co-beta-hydroxyvalerate); polygluconate; poly(beta-hydroxypropionate) (PHPA); poly(beta-dioxanone) (PDS); poly(delta-valerolactone); poly(epsilon-caprolactone); methylmethacrylate-N-vinylpyrrolidone copolymers; polyester amides; polyesters of oxalic acid; polydihydropyranes; poly(alkyl-2-cyanoacrylate); polyvinyl alcohol (PVA); polypeptides; poly(beta-maleic acid) (PMLA); poly(beta-alkanoic acid); poly(ethylene oxide) (PEO); polyanhydrides, polyphosphoester, and chitin polymers.

Each bioabsorbable polymer has a characteristic degradation rate in the body. For example, PGA and polydioxanone are relatively fast-bioabsorbing materials (weeks to months), whereas PLA and polycaprolactone are a relatively slow-bioabsorbing material (months to years).

As a general rule, mechanical properties improve with increasing molecular weight. For instance, the strength and modulus of PLA generally increases with increasing molecular weight. Degradation time, however, generally increases with increasing initial molecular weight (i.e., a stent made of a low molecular weight polymer will, as a general rule, be bioabsorbed before a stent made of a high molecular weight polymer), which may or may not be a desirable effect, depending on the application. Of course, bioabsorption time can be decreased by proper polymer selection as noted above.

The crystallinity of the polymeric material will also affect the mechanical properties as well as the degradation rate. For example, materials consisting of polyglycolide or of poly-L-lactide are known to have some degree of crystallinity, while those formed of DL-lactide are reportedly amorphous. The desired degree of crystallinity is adjusted in some embodiments by blending amorphous polymers with crystalline polymers. In certain beneficial embodiments of the invention, the filaments are formed from semi-crystalline polymeric materials with crystallinities or at least 0.1%, and preferably ranging from 0.1 to 0.2 to 0.5 to 1 to 2 to 10 to 20%, as measured with a differential scanning calorimeter (DSC) in accordance with the procedures of ASTM D3417. Differential scanning calorimetry can also be used to measure the glass transition temperature and melting point of the polymeric materials, as well as other properties.

Although stents constructed of bioabsorbable polymers typically have a larger profile when placed on a delivery catheter (and thus when in a body lumen) than certain metal stents (to compensate for the lower strength of the polymers relative to certain metals), stents constructed of bioabsorbable polymers can provide certain advantages relative to metal stents, including natural decomposition into non-toxic chemical species over a period of time. For example, bioabsorbable PLA and PGA materials are degraded in vivo through hydrolytic chain scission to lactic acid and glycolic acid, respectively, which can then be converted to $CO_2$ and then eliminated from the body by respiration, if necessary.

The oriented filaments of the present invention are subjected to one or more solid-state processing steps to give the molecules and/or fibrils within the filaments the desired helical orientation, which can thought of as a combination of longitudinal and twisting orientations. This is done to improve both the bending and torsional rigidity of the filaments relative to filaments containing non-oriented polymeric material, which in turn improves the properties of stents that contain the filaments, providing them, for example, with one or more of the following properties: increased radial force, decreased filament diameter for a given stent size, improved resistance to creep, and increased material selection due to improvement in properties.

Longitudinal orientation can be provided using a number of solid-state processes including solid-state extrusion, solid-state die drawing and solid-state rolling. As the name suggests, solid-state processing is performed at temperatures below the melting point of the material being processed, with typical temperatures being 60 to 90° C. for materials such as PLLA. As a general rule, the tensile strength of the filaments increases with lower draw temperatures and higher draw ratios.

In solid-state extrusion, a polymer preform (e.g., a billet or other preform such as a rod) is forced through a die (e.g., using a ram) or a series of dies. In die drawing, on the other hand, the preform is pulled through a die (typically a converging die) or a series of dies. Hence, die drawing is closely related to solid-state extrusion, except that the material is pulled, rather than pushed, through the die. The material is commonly spooled onto what is called a "drawing block" in die drawing.

During rolling, the preform is placed between opposing rolls (e.g., two opposing rollers, each with a groove having a semicircular cross-sectional profile), which rotate in opposite directions and reduce the diameter of the filament. The force can be generated, for example, by driving the wheels, by pushing the material through the wheels or by pulling the material through the wheels.

Each of these processes results in plastic deformation of the material, which is accompanied by a decrease in diameter, an increase in length, and an increase in the degree of longitudinal orientation of the polymer chains/fibrils within the material being processes. The increase in length is sometimes referred to as the "draw ratio," although this term can be used in reference to processes that are not technically "draw" processes, including extrusion and rolling, so long as the material is plastically deformed as described above. The draw ratio can be expressed in various ways, for example, in terms of the velocity at which the material emerges from the die or roller (or the total length of the material emerging), divided by the velocity at which the material enters the die or roller (or the total length of the material entering). Overall draw ratios on the order of 3 to 10 are typical.

The twisting orientation can be introduced to the material during the elongation process, for example, by rotating the preform, rotating the die or rollers, or rotating the take-up mechanism during processing. This facilitates continuous processing. Alternatively, the ends of the preform or the resulting filament can be fixed, and one or both fixed ends rotated at solid-state processing temperatures such as those described above, thereby providing molecules/fibrils with a twisted orientation.

Where the material is heated during orientation, cooling rates may vary depending on how the twist is imparted to the filament and may vary from minutes to hours at room temperature, post drawing. Annealing may also be advantageous, for example, between 65 and 90° C., post drawing. One of ordinary skill in the art can readily determine satisfactory cooling and or annealing conditions.

Once oriented filaments are provided, stents can be formed using various wire forming techniques known in the stent art, such as coiling techniques or weaving techniques (e.g., braiding or knitting).

As a specific example, in some embodiments, the filaments are fashioned into a tubular stent structure while in a cooled state and subsequently annealed at between 90 and 100° C. for a period of 10 to 15 minutes.

In some embodiments where the filaments themselves are formed into helices, overall orientation of the helical filament is oriented in the same direction as the helices at the molecular/fibril level; in other instances the helical filament is oriented in a direction opposite to that of the helices at the molecular/fibril level; in still order instances, some helical filaments are oriented in a direction opposite to that of the helices at the molecular/fibril level, and some are oriented in the same direction.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. A stent comprising a filament which has a longitudinal axis and which comprises an oriented bioabsorbable polymeric material, wherein polymer molecules within said bioabsorbable polymeric material have a helical orientation which is aligned with respect to the longitudinal axis of the filament, and wherein said stent is at least partially bioabsorbed by a patient upon implantation or insertion of the stent into the patient.

2. The stent of claim 1, wherein said filament is helically wound along at least a portion of the length of said stent.

3. The stent of claim 1, wherein said stent comprises a plurality of said filaments.

4. The stent of claim 3, wherein said plurality of said filaments are helically wound along at least a portion of the length of said stent.

5. The stent of claim 4, wherein a plurality of said filaments are helically wound in a first direction and a plurality of said filaments are helically wound in an opposite direction.

6. The stent of claim 1, wherein said filament is a braided filament.

7. The stent of claim 3, wherein said plurality of said filaments are braided and helically wound along at least a portion of the length of said stent.

8. The stent of claim 1, wherein said filament is a knitted filament.

9. The stent of claim 1, wherein said plurality of said filaments are knitted filaments.

10. The stent of claim 1, wherein said oriented bioabsorbable polymeric material comprises a single bioabsorbable polymer or a blend of bioabsorbable polymers.

11. The stent of claim 1, wherein said oriented bioabsorbable polymeric material comprises a polymer selected from poly($\alpha$-hydroxy acid) homopolymers, poly($\alpha$-hydroxy acid) copolymers and blends thereof.

12. The stent of claim 1, wherein said oriented bioabsorbable polymeric material comprises a polymer selected from polyglycolide, poly-L-lactide, poly-D-lactide, poly-DL-lactide, and blends thereof.

13. The stent of claim 1, wherein said oriented bioabsorbable polymeric material has a crystallinity ranging from 0.1 to 20%.

14. The stent of claim 1, wherein said filament comprises a core of said oriented bioabsorbable polymeric material.

15. The stent of claim 1, wherein said filament comprises a coating of said oriented bioabsorbable polymeric material.

16. The stent of claim 1, wherein said filament comprises a therapeutic agent.

17. The stent of claim 1, wherein said stent is selected from a coronary vascular stent, a peripheral vascular stent, a urethral stent, a ureteral stent, a biliary stent, a tracheal stent, a gastrointestinal stent and an esophageal stent.

* * * * *

UNITED STATES PATENT AND TRADEMARK OFFICE
CERTIFICATE OF CORRECTION

PATENT NO. : 7,594,928 B2  Page 1 of 1
APPLICATION NO. : 11/436067
DATED : September 29, 2009
INVENTOR(S) : Headley, Jr. et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 227 days.

Signed and Sealed this

Twenty-eighth Day of September, 2010

David J. Kappos
*Director of the United States Patent and Trademark Office*